United States Patent
Scarborough (10) Patent No.: US 9,066,994 B2
(45) Date of Patent: Jun. 30, 2015

(54) DEMINERALIZED CANCELLOUS STRIP DBM GRAFT

(75) Inventor: Nelson L. Scarborough, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1537 days.

(21) Appl. No.: 11/515,087

(22) Filed: Aug. 31, 2006

(65) Prior Publication Data

US 2008/0058953 A1   Mar. 6, 2008

(51) Int. Cl.
| | |
|---|---|
| *A61F 2/28* | (2006.01) |
| *A61L 27/36* | (2006.01) |
| *A61L 27/48* | (2006.01) |
| *A61L 31/00* | (2006.01) |
| *A61L 31/12* | (2006.01) |

(52) U.S. Cl.
CPC ....... *A61L 27/365* (2013.01); *A61F 2002/2835* (2013.01); *A61L 27/3608* (2013.01); *A61L 27/3683* (2013.01); *A61L 27/48* (2013.01); *A61L 31/005* (2013.01); *A61L 31/129* (2013.01)

(58) Field of Classification Search
USPC ............ 623/23.6–23.63, 11.11, 16.11, 23.48, 623/23.5, 23.51, 23.56, 919, 923
See application file for complete search history.

(56) References Cited

U.S. PATENT DOCUMENTS

| | | | |
|---|---|---|---|
| 4,902,296 A | 2/1990 | Bolander et al. | |
| 5,112,354 A | 5/1992 | Sires | |
| 5,368,859 A * | 11/1994 | Dunn et al. | 424/426 |
| 5,439,684 A * | 8/1995 | Prewett et al. | 424/422 |
| 5,876,452 A | 3/1999 | Athanasiou et al. | |
| 6,027,742 A * | 2/2000 | Lee et al. | 424/422 |
| 6,180,606 B1 | 1/2001 | Chen et al. | |
| 6,189,537 B1 | 2/2001 | Wolfinbarger, Jr. | |
| 6,305,379 B1 | 10/2001 | Wolfinbarger, Jr. | |
| 6,332,779 B1 | 12/2001 | Boyce et al. | |
| 6,372,257 B1 | 4/2002 | Marchosky | |
| 6,458,375 B1 | 10/2002 | Gertzman et al. | |
| 6,478,825 B1 * | 11/2002 | Winterbottom et al. | 623/23.63 |
| 6,548,080 B1 | 4/2003 | Gertzman et al. | |
| 6,616,698 B2 | 9/2003 | Scarborough | |
| 6,652,593 B2 | 11/2003 | Boyer, II et al. | |

(Continued)

FOREIGN PATENT DOCUMENTS

| | | |
|---|---|---|
| WO | 0205750 A2 | 1/2002 |
| WO | 03030956 A2 | 4/2003 |
| WO | WO 2004/017915 A2 | 3/2004 |

OTHER PUBLICATIONS

International Search Report and Written Opinion for European Application No. PCT/US2007/076948 mailed on Feb. 9, 2009.

(Continued)

*Primary Examiner* — David Isabella
*Assistant Examiner* — Suba Ganesan
(74) *Attorney, Agent, or Firm* — Sorell Lenna & Schmidt LLP (57) ABSTRACT

An osteoimplant includes at least partially demineralized cancellous bone as a substrate, which is impregnated with demineralized cortical bone matrix (DBM). The implant may include a binding agent to adhere the DBM to the cancellous bone substrate, and may also include a soft tissue barrier that covers a portion of the external surface of the implant. The cancellous bone substrate may be selectively demineralized, so as to provide regions with greater malleability, and other regions with greater structural properties.

21 Claims, 4 Drawing Sheets

(56) References Cited

U.S. PATENT DOCUMENTS

| | | |
|---|---|---|
| 6,761,739 B2 | 7/2004 | Shepard |
| 6,776,800 B2 | 8/2004 | Boyer, II et al. |
| 6,808,585 B2 | 10/2004 | Boyce et al. |
| 6,855,169 B2 | 2/2005 | Boyer, II et al. |
| 6,863,694 B1 | 3/2005 | Boyce et al. |
| 7,001,430 B2 | 2/2006 | Mills et al. |
| 7,001,551 B2 | 2/2006 | Meredith |
| 7,019,192 B2 | 3/2006 | Gertzman et al. |
| 7,045,141 B2 | 5/2006 | Merboth et al. |
| 7,097,792 B2 * | 8/2006 | Lin et al. .................. 264/42 |
| 2001/0014831 A1 | 8/2001 | Scarborough |
| 2001/0031254 A1 * | 10/2001 | Bianchi et al. .............. 424/93.7 |
| 2001/0038848 A1 | 11/2001 | Donda et al. |
| 2002/0016633 A1 * | 2/2002 | Lin et al. .................... 623/17.11 |
| 2002/0035401 A1 | 3/2002 | Boyce et al. |
| 2002/0177903 A1 * | 11/2002 | Geistlich et al. ........... 623/23.72 |
| 2003/0009235 A1 | 1/2003 | Manrique et al. |
| 2003/0028197 A1 * | 2/2003 | Hanson et al. .............. 623/17.16 |
| 2003/0036800 A1 | 2/2003 | Meredith |
| 2003/0143258 A1 | 7/2003 | Knaack et al. |
| 2003/0185803 A1 | 10/2003 | Kadiyala et al. |
| 2003/0206937 A1 | 11/2003 | Gertzman et al. |
| 2003/0228288 A1 | 12/2003 | Scarborough et al. |
| 2004/0078078 A1 | 4/2004 | Shepard |
| 2004/0091462 A1 | 5/2004 | Lin et al. |
| 2004/0102850 A1 | 5/2004 | Shepard |
| 2004/0197373 A1 | 10/2004 | Gertzman et al. |
| 2005/0055098 A1 | 3/2005 | Zdeblick et al. |
| 2005/0152880 A1 | 7/2005 | Mills et al. |
| 2005/0281856 A1 | 12/2005 | McGlohorn et al. |
| 2006/0013857 A1 | 1/2006 | Kronenthal |
| 2006/0030948 A1 | 2/2006 | Manrique et al. |
| 2006/0051427 A1 | 3/2006 | Talton et al. |
| 2006/0093640 A1 | 5/2006 | Duneas |
| 2006/0147545 A1 | 7/2006 | Scarborough et al. |
| 2006/0148704 A1 | 7/2006 | Schense et al. |

OTHER PUBLICATIONS

"OsteoSponge Create Possibilities", www.bacterin.com, Belgrade, MT, pp. 1-4.

* cited by examiner

DEMINERALIZED CANCELLOUS STRIP DBM GRAFT

FIELD OF THE INVENTION

The present invention relates to grafts that aid in the healing of bone. More particularly, the instant invention discloses cancellous bone, which is completely or partially demineralized, impregnated with demineralized bone matrix (DBM) for use as a grafting material.

BACKGROUND OF THE INVENTION

Grafts that aid in the healing of damaged bone are a relatively old technology that have undergone substantial growth in light of recent advances in medicine and biology. Improved understanding of osteoinductive and osteoconductive properties of certain materials has enabled the design of implants of ever-increasing efficacy. Recent examples include U.S. Pat. No. 7,045,141 to Merboth et al., entitled "Allograft Bone Composition Having a Gelatin Binder"; U.S. Pat. No. 6,808,585 to Boyce et al., entitled "Osteogenic Implant Derived From Bone"; U.S. Pat. No. 6,548,080 to Gertzman et al., entitled "Method for Partially Demineralized Cortical Bone Constructs"; and U.S. Pat. No. 6,776,800 to Boyer, II et al., entitled "Implants Formed with Demineralized Bone," all of which are incorporated herein by reference. Absorbable Collagen Sponge ("ACS"), by Integra LifeSciences Corporation (Plainsboro, N.J.), and Mastergraft® Matrix, by Medtronic Sofamor Danek (Memphis, Tenn.), are specific examples of grafts currently available on the market.

Many of these implants are easily contourable, but do not provide any structural support at the implant site. Structural support ranges from the ability to resist the tendency for compression of the graft by local tissues (space maintenance), to the ability to be weight bearing. There exist numerous situations in which it is desirable to have an implant that both aids in the re-growth of the bone at the implant site while also providing structural support, which are so-called structural implants. A drawback of structural implants is that the mechanical strength that they impart necessarily means that they tend to be difficult to contour to the geometry of the implant site. Additionally, structural implants tend to be less readily remodeled than their non-structural counterparts.

It is therefore desirable to provide an osteoimplant that provides structural (space maintaining and/or weight bearing) capabilities, yet which may be readily contourable, and which provides superior osteoinductive, osteoconductive and re-absorption properties.

SUMMARY OF THE INVENTION

One aspect of the invention provides an osteoimplant that includes at least partially demineralized cancellous bone as a substrate, which is impregnated with demineralized cortical bone matrix (DBM). In certain embodiments, the implant includes a binding agent to adhere the DBM to the cancellous bone substrate. In other embodiments, the implant further includes a soft tissue barrier that covers a portion of the external surface of the implant. The cancellous bone substrate may include a first region of lesser or no demineralization, and a second region of greater or substantially complete demineralization.

Another aspect of the invention provides a method for forming an osteoimplant. The method comprises impregnating a cancellous bone substrate with demineralized cortical bone matrix (DBM). The cancellous bone substrate is at least partially demineralized. In one embodiment, the impregnation process includes forming a slurry that includes the DBM, and contacting the cancellous bone substrate with the slurry. In another embodiment, the impregnation process includes contacting the cancellous bone substrate with a dry, powder form of the DBM. In certain embodiments, the method further includes performing a binding process to cause the DBM to bind to the at least partially demineralized cancellous bone substrate. In a specific embodiment, this binding process comprises heating the cancellous bone substrate to a temperature that is between about 42° C. and 50° C. In another specific embodiment, the binding method comprises impregnating the at least partially demineralized cancellous bone substrate with a binding agent. The instant method may further include coating the exterior surface of the cancellous bone substrate with a soft tissue barrier.

DETAILED DESCRIPTION

Figure 1:
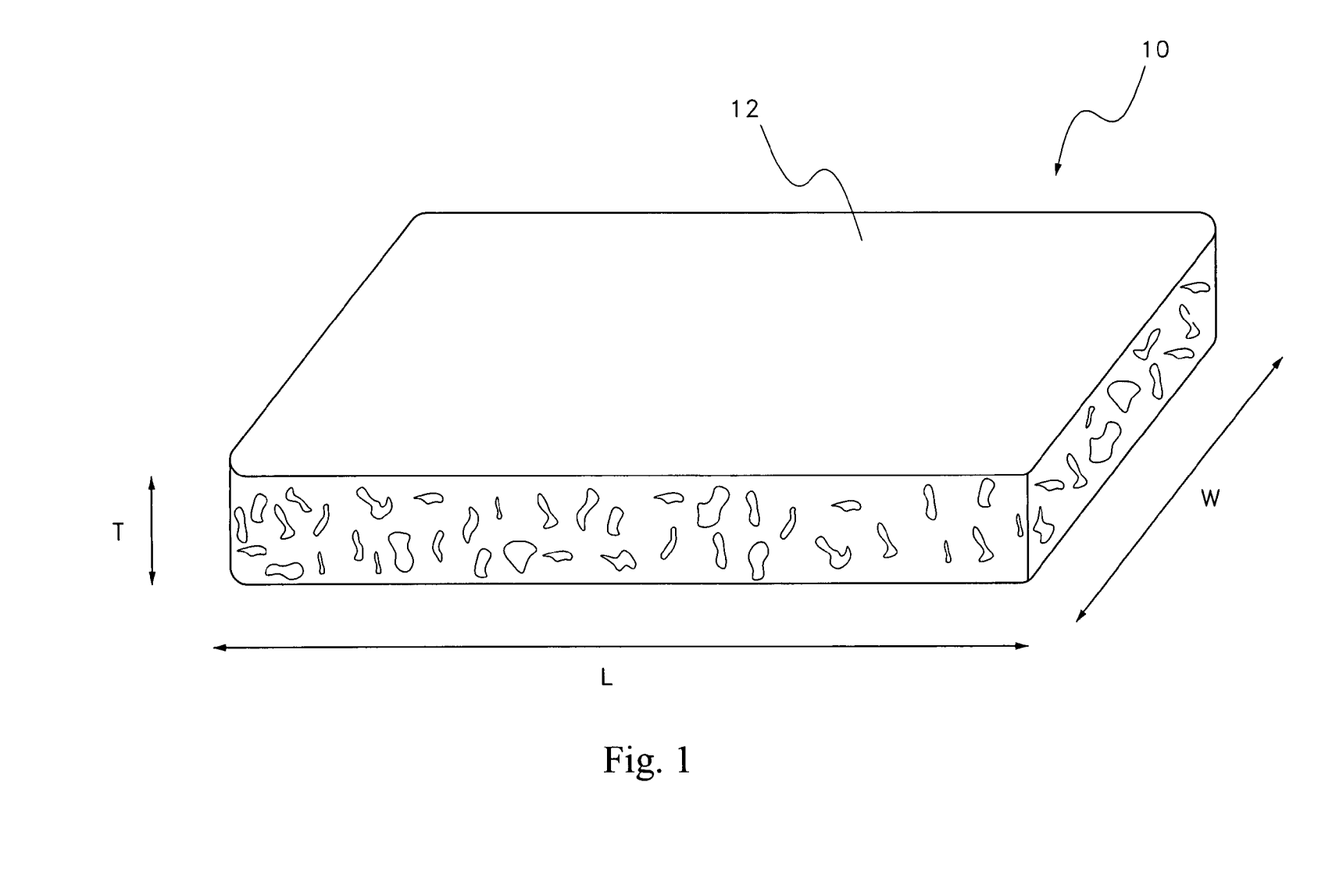
FIG. 1 is a perspective view of an example osteoimplant.

An exemplary osteoimplant 10 of the present invention is depicted in FIG. 1, and comprises as a substrate a cancellous bone segment 12. The cancellous bone segment 12 may be pre-shaped for a specific target region, or, as shown in FIG. 1, may be provided in a standard shape that may be later tailored by the physician for the particular requirements of the implant site. For example, the cancellous bone segment 12 may have a length L of 4 to 5 cm, a width W of 1.5 to 2.0 cm, and a thickness T of about 5 mm. In alternative embodiments, the cancellous bone segment 12 may be shaped in the form of a strip, a cylinder, or one or more demineralized cubes that may later be used to make a putty or grout. Of course, the shape need not be geometrically or site-specific perfect, and variations from a target shape are certainly possible, given the pliant nature of the graft 10. Any suitable method may be used to shape the cancellous bone segment 12, and may be performed before or after the cancellous bone segment 12 is partially or wholly demineralized.

The cancellous bone segment 12 may be from any source, but is preferably allogenic. Cancellous bone is used because it is readily absorbed into the surrounding bone of the implant site, and has superior osteoconductive properties. The cancellous bone segment 12 may be derived from cancellous bone from long bone sites, allowing for adequate anatomical dimensions for the intended final graft form. For grafts 10 intended to be used in procedures such as posterolateral spine fusion, the length of the segment 12 of cancellous bone is approximately 4 cm to 5 cm long. Segments 12 of this size obtained from allogeneic sources will generally be obtained from distal femur or proximal tibia anatomical sites. Grafts 10 of smaller dimensions intended for other applications may be obtained from any suitable anatomic location where cancellous bone with the proper characteristics is available.

The cancellous bone segment 12 acts as a porous matrix with interconnected pores, allowing for access throughout the porosity; that is, relatively few of the pores end in 'blind alleys.' Preferentially, the pore size of the cancellous matrix may be selected for the intended application, as the pore size can range depending on the anatomical location, as well as the patient age, health and other variables. Generally, cancellous bone immediately below the cartilage surface (subchondral bone) of a joint is more dense than that which is deeper within the metaphyseal region of the bone. By selecting the appropriate cancellous porosity, the matrix can be controlled to allow for the quantity of DBM which can be added, as well as the particle size of the DBM being impregnated. The porosity is also inversely related to the structural strength of the matrix, i.e. highly porous cancellous bone is weaker than dense cancellous bone.

The DBM and cancellous bone from allogeneic donors may be recovered and processed according to FDA and AATB (American Association of Tissue Banks) standards. Broadly, this involves donor consent, screening for communicable disease, processing to remove extraneous tissues under aseptic conditions to avoid introduction of contamination, demineralizing the components (DBM and cancellous) as required, and then forming the final graft 10. For allogeneic tissues, the DBM and cancellous matrix 12 may be obtained from the same donor. This may require significant logistical planning to obtain appropriate proportions of the cancellous and DBM components. Additionally, care should be taken when selecting the porosity of the cancellous bone 12 for the intended application, as significant variations exist both between individual donors and between anatomical regions from the same donor.

It is also anticipated that the current invention may use bone from xenogeneic sources as well, of course taking into consideration anatomical nuances and appreciating the potential immunogeneic issues.

Processing of the graft 10 may be performed under aseptic conditions such that the final graft 10 is sterile and does not require a terminal sterilization procedure. Alternatively, the graft 10 may be processed under less rigorous conditions and terminal sterilization used to achieve sterility. Various methods of terminal sterilization may be used (such as gamma or electron beam irradiation, ethylene oxide, etc.), but should be controlled to ensure the final graft 10 maintains appropriate biological characteristics for supporting bone growth.

The graft 10 can be constructed into a variety of shapes, sizes, porosities, structural capabilities, etc., for the intended application. An example above describes posterolateral spine fusion grafts, which are designed to span the transverse processes between adjacent lumbar vertebrae, which is a distance of approximately 3-5 cm. Another application for the graft 10 involves use in interbody 'cages' for spinal interbody fusion. In this instance, the graft 10 is preferably compressible to fit into the cage, and subsequently will tend to return to its precompression form to fill the space available. This property of being compressible and then returning to original shape has benefits in that it will fill voids effectively and provide a contiguous matrix for bone formation. This tendency helps overcome the relatively poor ability of bone to fill empty spaces, preferring to grow where a supporting matrix exists.

The cancellous bone segment 12 is at least partially demineralized, and may be fully demineralized. The term "partial demineralization" means that anywhere from 5% to 90% of the original mineral content of the cancellous bone has been removed. "Completely demineralized" means that about 90% to 100% of the original mineral content of the cancellous bone has been removed. Methods that provide for the complete or partial demineralization of cancellous bone are known, and broadly involve chemically processing cancellous bone with hydrochloric acid, chelating agents, electrolysis or performing other treatments to remove all or a portion of the minerals contained within the natural bone, leaving behind collagen fibers. The cancellous bone segment 12 thus provides a type 1 collagen sponge with interconnected pores, with optionally some mineral content depending upon the amount of demineralization performed. The amount of demineralization of the cancellous bone segment 12 will depend upon the desired properties of the implant 10. Greater demineralization enables faster remodeling of the implant 10, and provides greater abilities to mold the graft 10 into the defect site. However, the greater the demineralization of the cancellous bone segment 12, the less compression resistance the implant 10 will have, with a corresponding reduction in structural properties.

The osteoimplant 10 further comprises demineralized cortical bone matrix (DBM), with which the at least partially demineralized cancellous bone segment 12 is impregnated. DBM is basically finely ground, demineralized cortical bone, and is known to have osteoinductive properties. Because cancellous bone is highly porous, the cancellous bone segment 12 provides a highly porous substrate into which the finely ground DBM may be disposed. That is, the pores of the cancellous bone segment 12 may be populated with the DBM particles. It is expected that the implant 10 will have a weight to weight ratio of DBM to cancellous bone from about 2 up to about 4, with a lyophilized moisture content of about less than 6%.

To insure that the DBM can penetrate into the cancellous bone segment 12, the particle size of the DBM should be less than the pore size of the partially or completely demineralized cancellous bone segment 12. However, the DBM should not be so finely ground that it is resorbed by the host before it can act as a scaffold to support bone growth. The rate at which this process occurs is somewhat variable depending on many factors, but generally the graft needs to act as a scaffold for at least several weeks. Grafts which resorb too rapidly or which are resistant to remodeling are less effective in supporting bone formation. It is expected that the average particle size of the DBM should be between 50 and 900 µm, and more preferably between 100 and 500 µm. However, it will be appreciated that these values may change based upon the structural characteristics of the cancellous bone segment 12. The denser the cancellous bone substrate 12 is, the greater the structural strength that the substrate 12 provides. Dense cancellous bone has pore sizes that are relatively smaller than less dense cancellous bone, and so the particle size of the DBM may have to be adjusted accordingly. For example, if the substrate 12 is made from cancellous bone that is relatively dense, then finer particle sizes for the DBM will be required, perhaps on the order of 50 µm to 250 µm. Alternatively, if the cancellous bone substrate 12 is relatively porous, then larger particle sizes may be used, such as DBM particles from 100 µm to 900 µm in size.

DBM may be obtained as known in the art. For example, DBM may be produced by exposing cortical bone from long bones of allogeneic or xenogeneic origin to acidic conditions (eg. 0.5N HCl), chelating agents (EDTA, etc.) electrolysis, etc. These conditions enhance the solubilization of the native hydroxyapatite form of calcium phosphate and release it from the collagen based scaffold of bone. The bone is typically first ground or milled into a particulate form and sieved to control particle size prior to demineralization. This enhances the surface-to-volume ratio, and allows for greater contact between the bone and the demineralization agent, and subsequently more efficient demineralization. On the other hand, when demineralizing cancellous bone, the porosity allows access to the internal matrix, and the relatively thin spicules of bone are readily penetrated and demineralized.

One aspect of the present invention provides for selecting the cancellous bone substrate 12 based upon the load-bearing necessities of the target implant site. In situations where the graft 10 is to be implanted in locations that may experience loading, i.e., in structural applications of the graft 10, the use of a dense cancellous bone substrate 12 may be preferred, as such a substrate 12 provides for greater structural strength. On the other hand, for non-structural applications of the graft 10, less dense cancellous bone may be used for the substrate 12, as this allows for greater infusion of the substrate 12 with larger particle sizes of the DBM.

Various methods exist for providing an at least approximate quantification of the porosity of the cancellous bone segment 12. Some of these methods include classifications based upon density (weight per unit volume; requires prior cleaning to remove extraneous tissues, such as fat and blood); light transmission through a known thickness of cancellous bone (such as by holding the cancellous bone segment 12 up to a light source and looking through the segment 12); and mechanical testing (load resistance correlates with cancellous density). By selecting the porosity of the cancellous bone segment 12 and matching this porosity to the intended use, the properties of the final osteograft 10 can be well controlled.

It will be appreciated that the structural properties of the graft 10 may be further controlled by the amount of demineralization of the cancellous bone segment 12. For implants 10 requiring greater structural properties, it may be preferable to use cancellous bone segments 12 that are only partially demineralized (i.e., have a relatively higher mineral content), as these provide greater compression resistance. Alternatively, in situations in which the structural capabilities of the implant 10 are of lesser importance, it may be desirable to use as a substrate a cancellous bone segment 12 that has been substantially or completely demineralized, as such a substrate 12 provides superior remodeling properties, is easier to contour to the target site, and may also have larger pore sizes that can carry larger amounts of DBM at larger particle sizes so as to provide superior osteoinductive properties.

The following examples provide illustrations of various surgical uses of the graft 10 with various load bearing/space maintenance requirements, for which the structural properties of the graft 10 may be tailored accordingly, as explained above. As a first example, grafts 10 designed for placement within an interbody spine fusion cage are protected from loads by the cage, and so do not require load-bearing capabilities. The graft 10 inside and/or surrounding the cage needs to fill the void and maintain contact with the surrounding bone such that the entire space is filled with new bone. It may therefore be desirable to provide a completely demineralized substrate 12 to provide for maximum malleability and space-filling properties.

In the instance of a posterolateral spine fusion, the graft 10 is placed such that it spans the distance between the adjacent transverse processes. This application is not weight bearing, but the graft must be able to resist the forces imposed by the surrounding muscle layers. In this instance space maintenance is necessary to support bone formation with adequate volume to provide eventual integrity, to provide stabilization of the spine, and to be partly weight bearing. It may therefore be desirable to provide a substantially demineralized substrate 12 to allow for space-filling properties, while having sufficient mechanical properties to resist the loads imposed by the surrounding muscle layers. The demineralized substrate 12 may have, for example, from 5% to 50% residual calcium.

An example where more load bearing capabilities are required is ridge augmentation procedures for periodontal/oral maxillofacial indications. In this instance, the graft would preferentially provide adequate structural integrity to resist compression and volume reduction due to the loading imparted by gingival tissue forces, forces imposed by the tongue, and during mastication of food and oral contents. It may therefore be desirable to have a substrate 12 that has been only partially demineralized, rather than substantially or completely demineralized. These regions of partial demineralization may have, for example, 50% to 90% residual calcium. It may also be advantageous in this instance to have a graft where certain areas are relatively highly demineralized to allow flexibility, and other areas that are not demineralized or only partially so to maintain structural integrity. The regions of greater flexibility may have, for example, 10% or less of residual calcium. Such a graft 10 is not, however, intended for full loading bearing, as would be required for segmental loss of bone, such as due to complex tibial fractures. For these types of indications, the graft 10 should be supported by ancillary hardware, such as plates and screws, in many instances.

Figure 2A:
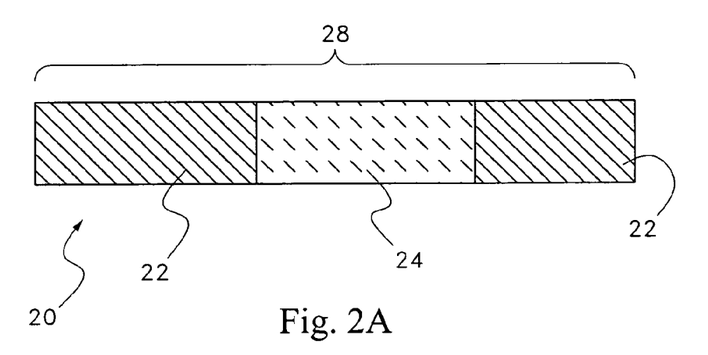
FIGS. 2A and 2B show a cross-sectional view of another osteoimplant.
Figure 2B:
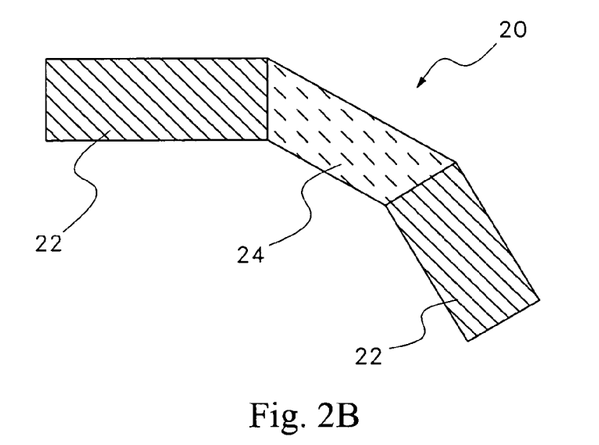

As indicated above, for certain target sites of the graft 10, it is desirable that the graft 10 be both easily contourable, yet also have structural properties. Typically, these two characteristics are mutually exclusive, as ease of contourability implies that the structural characteristics of the implant 10 must be rather weak, i.e., that the implant 10 be easily molded or formed to the contours of the implant site, and thus lack structural strength. Nevertheless, the present invention provides for implants that are contourable while simultaneously providing structural properties. An example implant 20, depicted in FIG. 2A, comprises a single cancellous bone segment 28 that has been selectively demineralized so as to provide a first region of greater mineralization 22 (i.e., lesser demineralization 22), and a second region of lesser mineralization 24 (i.e., greater demineralization 24). The first regions of greater mineralization 22 may be wholly or partially mineralized, and the second regions of lesser mineralization 24 may be wholly or partially demineralized. As with the implant 10, the cancellous bone segment 28 is impregnated with DBM. The one or more first regions of greater mineralization 22 provide structural characteristics, while the one or more second regions of lesser mineralization 24 are more flexible, and so provide for contourability. As shown in FIG. 2B, the structural regions 22 are capable of bending around the more flexible region 24, thus enabling the structural regions 22 to be contoured to the implant site. It will be appreciated that the implant 20 may have numerous regions of lesser and greater mineralization 22, 24, with various shapes, to provide the best contourability with the greatest amount of structural capabilities. An implant 20 with multiple first and second regions 22, 24 may be particularly suited, for example, in mandible reconstruction, in which both contouring and structural support are required of the osteoimplant.

Methods for providing bones with selective regions of greater and lesser demineralization are known. See, e.g., U.S. Pat. No. 6,652,593 to Boyer, II et al., entitled "Demineralized Bone Implants," incorporated herein by reference, which uses mechanical masks sealed against machined bone surfaces to provide selective demineralization of a bone substrate. With reference to FIG. 2A, an alternative method is to employ a bio-compatible wax, such as paraffin or bone wax, to coat the first regions 22 in which greater mineralization is desired. The wax ideally has a melting temperature that is less than 45° C. Once the first regions 22 have been coated with the wax, the entire bone segment 28 is immersed into a demineralizing agent. The wax covering first regions 22 protects those regions 22 from the demineralizing agent; only the second regions 24 are exposed to the demineralizing agent. Despite the relative porosity of the cancellous bone segment 28, the kinetics of the diffusion process make it so that slow pathways presented by regions 22 are relatively unimportant compared to fast pathways provided by regions 24, and so the masked regions 22 are relatively unaffected by the demineralization agent. After a predetermined amount of time, the substrate 28 is removed from the agent, rinsed, and then heated and further rinsed to remove the wax covering the first regions 22. If it is desired that the first regions 22 also undergo a certain amount of demineralization, then the substrate 28 may again be immersed into a demineralizing agent, which will result in the partial demineralization of the first regions 22, as they are now unprotected by the wax, and further demineralization of the second regions 24. The end product will yield a cancellous bone substrate 28 with regions of greater demineralization 24, and regions of lesser or no demineralization 22. It will be appreciated that other methods, apart from wax, may be employed to achieve masking of the regions of lesser demineralization 22. For example, masking may be provided by regions where the native fat is not removed, or other hydrophobic reagents; alternatively, selective application of the demineralizing agent may be employed (i.e., dripping acid on some areas, and leaving other areas dry).

Once a substrate of partially or completely demineralized cancellous bone 10, 20 has been provided, it is necessary to impregnate the substrate 10, 20 with the DBM. As indicated earlier, the DBM may be milled to a particle size that is less than, on average, the average pore size of the substrate 10, 20, so that the DBM may infuse the pores of the substrate 10, 20. Various methods may be employed to impregnate the substrate with the DBM, which are described in the following.

In one embodiment, a slurry is made of the DBM, which has been milled down to an appropriate particle size. Water or a saline solution, for example, may be used to form a slurry. This slurry is then coated over the substrate 10, 20. The substrate 10, 20 may optionally be vibrated and/or rotated or centrifuged to encourage the slurry to migrate into the pores. When the pore sizes are particularly small, air within the pores can present a substantial impediment to the entry of the slurry. Consequently, prior to administering the slurry, it may be desirable to subject the substrate 10, 20 to at least a mild vacuum to partially or wholly evacuate the air from the pores. A mild vacuum can evacuate bubbles without boiling off fluid within the slurry.

When making a slurry of the DBM, it may be desirable to select a solution that does not cause swelling of the DBM particles, or which prevents swelling of the DBM particles, as swelling may prevent the DBM particles from seating inside the substrate pores. For example, a solution of ethanol may be used to create a slurry with the DBM. Other types of solutions such as hypertonic aqueous salt or sugar solutions may also be advantageous to achieve this result.

Figure 3:
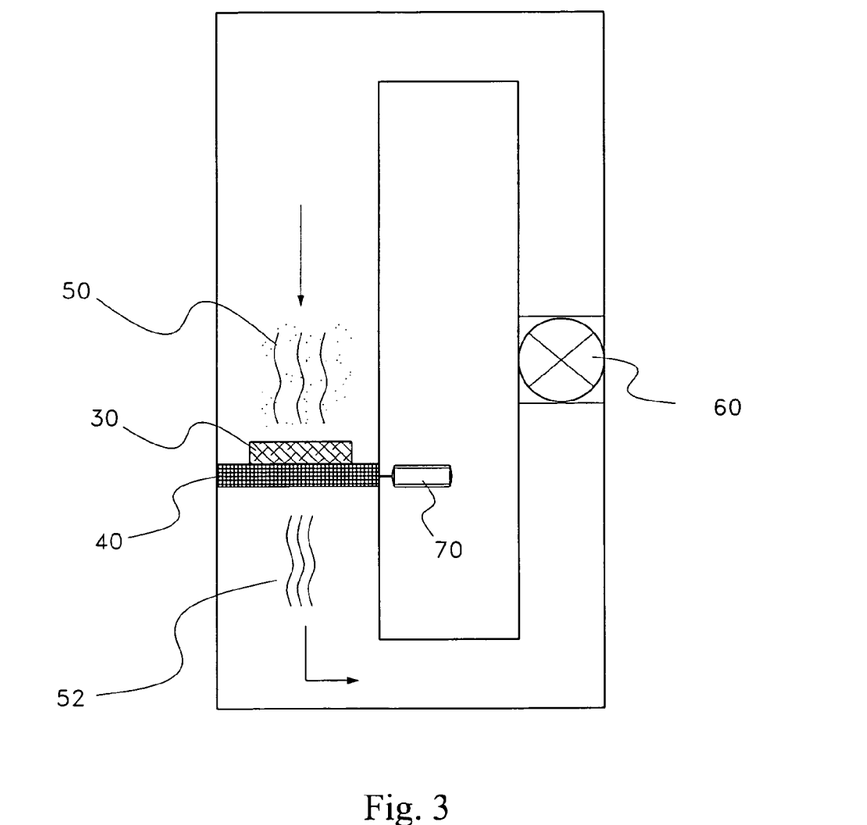
FIG. 3 illustrates an example DBM impregnation procedure for an osteoimplant.

In certain embodiments, the substrate 10, 20 may be placed upon a sieve, and then pressure may be applied to the DBM slurry to facilitate its injection into the pores of the substrate 10, 20. An example configuration is shown in FIG. 3, in which a partially or wholly demineralized cancellous bone segment 30 is placed upon a sieve 40. The sieve 40 has numerous openings, which may be less than 100 μm in size. The openings of the sieve 40 are sized to prevent the DBM particles from passing through the sieve 40. A pump 60 applies pressure to the DBM slurry 50, so that the slurry 50 is forced onto and into the substrate 30. The DBM particles remain behind on the substrate 30 and sieve 40, while the carrier solution 52 may pass back around to the pump or be discarded 60. An optional vibrating mechanism 70 may be used to vibrate the sieve 40, and hence the substrate 30, to further facilitate the diffusion of the DBM slurry 50 into the substrate 30. The substrate 30 may be periodically rotated so that various surfaces of the substrate 30 directly face the incoming slurry 50. Pressure and flow rates required to achieve impregnation of the DBM within the substrate 30 are easily attainable, and it will be appreciated that several approaches apart from the system depicted in FIG. 3 may be used. For example, a system as simple as placing the slurry into a syringe with a relatively large opening and manually pressurizing the syringe may be used. Alternatively, mechanical means, such as peristaltic pumps or other devices, may be used.

The above impregnation methods may also be employed with DBM in a powdered state. For example, dry, powdered DBM may be coated onto the cancellous bone substrate, or, using a configuration as depicted in FIG. 3, may be continuously blown into the substrate 30. The substrate may be vibrated, centrifuged or other mechanical means used to further encourage the powdered DBM to migrate into the pores.

Other impregnation methods may include filtration, centrifugation, and manually working the DBM into the substrate, such as by squeezing the substrate in a DBM slurry so that the slurry is pulled into the substrate like water into a sponge.

Once the cancellous bone substrate has been impregnated with the DBM, it may be desirable to perform a binding process to ensure that the DBM remains bound within the substrate. Various methods may be employed to perform this binding process, some of which are described in the following.

Because the DBM is ideally embedded within the pores of the cancellous bone substrate, if the DBM particles are caused to swell in size, they may effectively wedge themselves within the pores. Hence, one binding method entails soaking the DBM-impregnated substrate in an appropriate solution that causes the DBM particles to swell. Simply hydrating the DBM, for example, will cause the DBM particles to swell in size. Other suitable solutions include alginate, glycerol, sugars, oils, lipids, proteins such as gelatin, etc. Materials which are sticky in texture may also assist in the adherence of the DBM. This method may be particularly effective when a dry, powdered form of the DBM was used during the impregnation process, or, if during slurry processing, a suitable chemical had been used to prevent swelling of the DBM.

As previously described, the partially or wholly demineralized cancellous bone substrate that the DBM impregnates forms a type 1 collagen sponge. When collagen is heated, the intermolecular bonds within the collagen create a somewhat sticky surface. Hence, in one embodiment, the DBM-impregnated substrate is heated to a temperature that is high enough to cause the collagen to become sticky, or tacky, but which is not so high as to cause decomposition of the osteoinductive proteins within the DBM, thereby causing the DBM particles to stick to the collagen in the substrate. In a specific embodiment, the cancellous bone substrate is heated to between about 40° C. and 55° C., and more preferably between about 42° C. and 45° C., for 15 to 60 minutes. Additionally, it may be desirable to hydrate the collagen prior to heating to enhance the binding. Alternatively, the heating step can be performed in a high-humidity chamber to allow for the binding to occur.

In alternative embodiments, excipients that have adhesive properties are employed to bind the DBM particles to the cancellous bone substrate. The DBM-impregnated substrate may be coated with a solution containing one or more adhesive substances to bind the DBM to the substrate. Suitable substances include sugars, such as dextrose, mannose, glucose, etc. Sugars may be additionally beneficial in that they may also enhance re-hydration of the implant due to their hydrophilic properties. Other substances include alginate; cross-linking agents, such as glutaraldehyde; agarose or other hydrophilic gels; agents that create ionic bonds, such as calcium chloride; agents that create polymeric bonds, such as polyglycolic acid, polylactic acid, etc.; or calcium sulfate and other similar compounds. It should be noted, however, that the extent of cross-linking should be tightly controlled to avoid the cross-linking agent, or the like, from becoming a barrier to cell ingrowth or causing denaturation of the osteoinductive proteins or alteration in the collagen components, which may adversely affect their biological properties.

In a specific embodiment, glycerol may be used as an excipient to bind the DBM to the cancellous bone substrate. After the DBM is packed into the substrate, a solution of glycerol and water may be used to wet the substrate. This will cause the DBM particles to swell, locking them into place within the substrate. The cancellous bone substrate may then by lyophilized to remove the excess water. The glycerol will remain behind, serving both to adhere the DBM particles to the substrate, and to cause the DBM particles to remain in a swollen state, and thus remain locked within the pores of the substrate. The glycerol is additionally beneficial as a wetting agent to speed the re-hydration of the bone graft, and also serves as a plasticizing agent, keeping the non-hydrated substrate supple.

It is expected that the invention implant will have utility in a diverse array of procedures, including posterolateral spinal fusion, interbody spine fusion, fracture repair, bone cyst filling, periodontal, cranial, containment of autograft, maxillofacial, and other procedures where bone grafting is desireable. To further extend the suitability of the instant invention to various procedures, the invention graft may be provided a soft-tissue barrier over a portion of its external surface to promote guided tissue regeneration. The concept of guided tissue regeneration as applied to osteoimplants is known. See, e.g., U.S. Pat. No. 6,332,779 to Boyce et al., entitled "Method of Hard Tissue Repair," which is incorporated herein by reference. The concern behind guided tissue regeneration is that soft tissue tends to migrate into and fill voids faster than bone. As a result, an osteoimplant may be invaded by soft tissue before the bone has had a chance to grow into the implant, frustrating the purpose of the implant. The solution is to create barriers to the soft tissue that prevent it from growing into the implant, while presenting no such barriers to the adjacent native bone. The native bone may then grow, unimpeded, into the implant.

Figure 4:
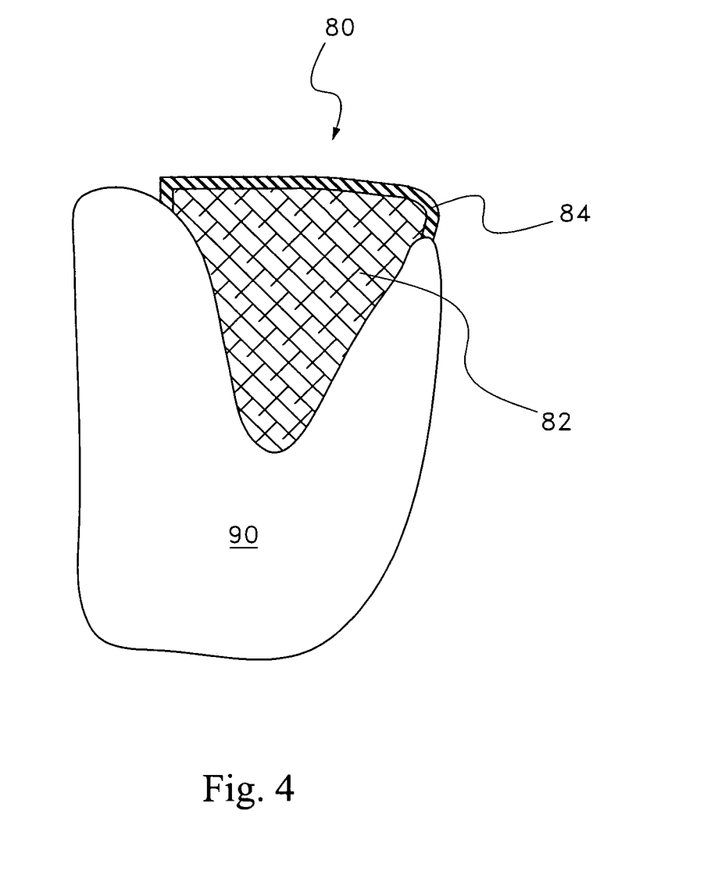
FIG. 4 illustrates guided tissue regeneration with an embodiment osteoimplant.

By way of example, an implant 80, used as a graft for an extraction socket, is shown in FIG. 4. The graft 80 comprises a partially or wholly demineralized cancellous bone substrate 82 that has been impregnated with DBM, and a soft tissue barrier 84 disposed along a portion of the outer surface of the implant 80 where contact is expected with soft tissue. The soft tissue barrier 84 is preferably made from a bio-degradable material, such as PLGA (poly(lactic-co-glycolic acid)), and blocks the ingrowth of soft connective tissue into the implant 80. Those portions of the implant 80 that are in contact with, or immediately adjacent to, the host bone 90 are not covered with the soft tissue barrier 84, so that the host bone 90 can migrate into the implant 80. The entire void filled by the implant 80 should thus eventually fill with native bone 90, and not be invaded by any soft tissue. It is further noted that the malleability, contourability, compressibility and subsequent expansion of the implant 80 permits the void in the native bone 90 to be filled without any substantial gaps.

The tendency for bone forming cells to preferentially migrate into a graft by expanding along osteoconductive surfaces makes continuity of the graft with the host bed an important characteristic. Another source of bone forming cells is from new blood vessels which form through an angiogenic response. Again, continuity of the graft and host bed established by an osteoconductive matrix is important for new bone formation. An example illustrating the challenge that is created when empty voids exist is the relative slowness of healing of boer removal of screws. These gaps, which are in the 3-6 mm range, can often remain unrepaired for extended periods of time, and in some instances are only filled by soft-tissue rather than bone. By providing an osteograft that may be closely tailored to the implant location, the present invention ensures that gap sizes remain at a minimum, and so improves bone growth into the implant, while optionally deterring soft tissue invasion.

One method of creating a barrier 84 to soft tissue ingrowth is to use relatively high heat (60 to 70° C.) to anneal the collagen on the surface where the barrier is desired. This process causes structural changes in the collagen resulting in a less porous structure that resists tissue ingrowth, as well as becoming more resistant to natural resorptive processes. Another method is to coat the surface with materials which are biocompatible, but resistant to penetration by soft tissue. Examples of these are fibrin glue, cyanoacrylate 'liquid sutures,' polymeric materials such as PLA or PGA; ceramic particles, such as sintered hydroxyapatite; bone wax, etc. The goal is for the surface to slow down the soft tissue invasion process enough to let the slower forming bone tissue 90 to form. The barrier 84 can then be resorbed through normal processes such that the final result is one where the entire graft 80 has been replaced with the appropriate native tissues, i.e. bone where it should be, soft tissue where it should be.

It is believed that the invention implant may be further impregnated with one or more bioactive substances to achieve additional medically useful ends. In particular, it is believed that the osteoimplant may be impregnated with one or more bioactive substances that further encourage bone growth. Examples include, but are not limited to, Bone Morphogenetic Proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βs), including TGF-β-1, TGF-β-2, and TGF-β-3, and inhibitors for tumor necrosis factor (e.g., anti-TNFα). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, which is incorporated herein by reference. The polynucleotides encoding the same may also be administered as gene therapy agents. The preferred bioactive substances are the recombinant human bone morphogenetic proteins (rhBMPs) because they are available in relatively unlimited supply and do not transmit infectious diseases. Most preferably, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al.

Implants of the present invention may be further impregnated with other bioactive substances, including cells (such as by working bone marrow aspirate or platelet rich plasma into the graft), anti-inflammatory compounds, antibiotics, autogenous graft material, and pain-reducing agents.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. An implant comprising a cancellous bone substrate and a demineralized cortical bone matrix (DBM) having a weight to weight ratio from 4 to 2, wherein the cancellous bone substrate has a porous matrix of interconnected pores, wherein the cancellous bone substrate is at least partially demineralized, wherein the DBM is in the form of particles having an average particle size between 50 µm and 900 µm and the average particle size of the DBM is less than an average pore size of the cancellous bone, wherein the porous matrix is impregnated with the demineralized cortical bone matrix (DBM) and the demineralized cortical bone matrix is embedded within the interconnected pores of the demineralized cancellous bone substrate, and wherein the embedded DBM particles are bound to the cancellous bone substrate, and a soft tissue barrier comprising a bone wax covering at least a portion of an external surface of the implant.

2. The implant of claim 1 wherein the embedded DBM particles are bound to the cancellous bone substrate with an adhesive substance comprising a sugar.

3. The implant of claim 2 wherein the portions of the implant that will contact or be immediately adjacent to host bone are not covered with the soft tissue barrier.

4. The implant of claim 3 wherein the average particle size is between 100 µm and 500 µm.

5. The implant of claim 2, wherein the sugar is mannose.

6. The implant of claim 1 wherein the at least partially demineralized cancellous bone comprises a first region of lesser or no demineralization, and a second region of greater or substantially complete demineralization.

7. The implant of claim 1 wherein the at least partially demineralized cancellous bone is shaped substantially as a strip, a cylinder, or a cube.

8. The implant of claim 1 wherein the demineralized cancellous bone substrate comprises from 5% to 50% residual calcium.

9. The implant of claim 1 wherein the demineralized cancellous bone substrate comprises from 50% to 90% residual calcium.

10. The implant of claim 9 wherein an average particle size of the DBM is between 100 µm and 500 µm.

11. The implant of claim 10 wherein the cancellous bone substrate is pre-shaped for a specific target region.

12. The implant of claim 1 wherein the cancellous bone substrate is shaped in a cube that may later be used to make a putty or grout.

13. An implant comprising:
a cancellous bone substrate;
and a demineralized cortical bone matrix (DBM) having a weight to weight ratio of 4 to 2 and having a particle size of 50 µm to 250 µm; and
a soft tissue barrier comprising a bone wax covering at least a portion of the external surface of the implant,
wherein the cancellous bone substrate has a porous matrix of interconnected pores and wherein the cancellous bone substrate is at least partially demineralized, wherein the average particle size of the DBM is less than an average pore size of the cancellous bone, wherein the porous matrix is impregnated with the demineralized cortical bone matrix (DBM) and the demineralized cortical bone matrix is embedded within the interconnected pores to the at least partially demineralized cancellous bone substrate, and wherein the embedded DBM particles are bound to the cancellous bone substrate.

14. The implant of claim 13 wherein the embedded DBM particles are bound to the cancellous bone substrate with an adhesive substance comprising a sugar.

15. The implant of claim 14 wherein the cancellous bone substrate is pre-shaped for a specific target region.

16. The implant of claim 14 wherein the cancellous bone substrate is shaped in a cube that may later be used to make a putty or grout.

17. The implant of claim 16 wherein the soft tissue barrier is made from a bio-degradable material.

18. The implant of claim 14, wherein the sugar is mannose.

19. The implant of claim 13 wherein the demineralized cancellous substrate comprises from 5% to 50% residual calcium.

20. The implant of claim 13 wherein the at least partially demineralized cancellous bone substrate comprises a first region of lesser or no demineralization, and a second region of greater or substantially complete demineralization.

21. The implant of claim 20 wherein the second region has greater flexibility than the first region.

* * * * *